US008497112B2

(12) United States Patent
Kistner et al.

(10) Patent No.: US 8,497,112 B2
(45) Date of Patent: Jul. 30, 2013

(54) METHOD FOR PRODUCING VIRAL VACCINES

(75) Inventors: Otfried Kistner, Vienna (AT); Christa Tauer, Vienna (AT); Noel Barrett, Klosterneuburg/Weidling (AT); Wolfgang Mundt, Vienna (AT)

(73) Assignees: Baxter International Inc., Deerfield, IL (US); Baxter Healthcare SA, Glattpark (Opfikon) (CH)

( * ) Notice: Subject to any disclaimer, the term of this patent is extended or adjusted under 35 U.S.C. 154(b) by 0 days.

(21) Appl. No.: 12/199,977

(22) Filed: Aug. 28, 2008

(65) Prior Publication Data

US 2009/0060950 A1 Mar. 5, 2009

Related U.S. Application Data

(60) Provisional application No. 60/966,724, filed on Aug. 28, 2007.

(51) Int. Cl.

| | |
|---|---|
| ***C12N 7/02*** | (2006.01) |
| ***C12N 7/04*** | (2006.01) |
| ***C12N 7/06*** | (2006.01) |

(52) U.S. Cl.
USPC ......... 435/239; 435/235.1; 435/236; 435/238

(58) Field of Classification Search
None
See application file for complete search history.

(56) References Cited

U.S. PATENT DOCUMENTS

| | | | | |
|---|---|---|---|---|
| 4,522,809 A | | 6/1985 | Adamowics et al. | |
| 6,048,537 A | | 4/2000 | Violay et al. | |
| 6,136,321 A | * | 10/2000 | Barrett et al. | 424/208.1 |
| 2004/0022808 A1 | * | 2/2004 | Colau et al. | 424/204.1 |
| 2006/0063261 A1 | * | 3/2006 | Pau et al. | 435/456 |
| 2006/0270017 A1 | | 11/2006 | Reiter et al. | |

FOREIGN PATENT DOCUMENTS

| | | |
|---|---|---|
| EP | 0514199 | 11/1992 |
| EP | 1057889 | 12/2000 |
| EP | 1724338 | 11/2006 |
| GB | 1498261 | 1/1978 |
| WO | WO-00/35481 | 6/2000 |
| WO | WO-02/09702 | 2/2002 |
| WO | WO 02/097072 A2 * | 12/2002 |

OTHER PUBLICATIONS

Gupta et al., An efficient method for production of purified inactivated Japanese encephalitis vaccine from mouse brains. *Vaccine.* 9(12): 865-7 (1991).

Kistner et al., Cell culture (vero) derived whole virus (H5N1) vaccine based on wild-type virus strain induces cross-protective immune response. *Vaccine.* 25(32): 6028-36 (2007).

International Search Report and Written Opinion of the International Searching Authority, European Patent Office, PCT/US2008/74559, dated Nov. 28, 2008.

* cited by examiner

*Primary Examiner* — Stacy B. Chen
(74) *Attorney, Agent, or Firm* — Marshall, Gerstein & Borun LLP

(57) ABSTRACT

The present invention provides a method for the manufacture of a preparation comprising virus antigens comprising
a) inoculation of cells with infectious virus in a fluid,
b) propagation of said virus in said cells,
c) collecting said propagated virus,
d) inactivating said collected virus, and
e) treating said inactivated virus with a detergent, resulting in a preparation comprising viral antigens.

22 Claims, 2 Drawing Sheets

METHOD FOR PRODUCING VIRAL VACCINES

FIELD OF THE INVENTION

The present invention relates to methods for producing viral vaccines.

DESCRIPTION OF THE RELATED ART

A vaccine is an immunogenic composition of an antigenic substance, e.g. the (non-infectious) pathogen such as a virus, its envelope, particles or its protein antigens. Administration or vaccination results in the immunization in a subject, e.g. a mammal such as a human, or a bird. The vaccination might cause a specific reaction to the vaccine and some minor inflammation, but this is generally much less detrimental than an infection of a fully viable virus which the vaccine is designed to prevent. The immune system of the subjects will adapt itself to specifically recognize the antigens of the vaccine and swiftly inactivate the pathogen after further exposure of the subject to the pathogen. Thus an increased resistance against the pathogen is achieved through vaccination.

For vaccine purposes a virus is conventionally cultivated on an adequate cell culture or generally cellular substrate. In the case of influenza, normally embryonated chicken eggs are used. The infectious viral harvest is collected and purified to remove unwanted non-viral cell constituents. In particular, in the case of vaccines derived from chicken substrates allergic reaction to chicken/egg proteins are possible in certain susceptible individuals.

An essential step in the production of viral vaccines is the inactivation of the infectious viruses. Formalin (an aqueous solution of formaldehyde) is the most frequently used inactivating agent in the manufacture of vaccines. It is usually used as a saturated aqueous solution with concentration of around 37% formaldehyde. Formaldehyde inactivates a virus by irreversibly cross-linking primary amine groups in surface proteins with other nearby nitrogen atoms in protein or DNA through a —$CH_2$-linkage. In particular these cross linkages could lead to bonds with non-viral substances and it is therefore necessary to perform some previous purification on the live infectious virus, since inactivation prior to purification would give rise to a large amount of irreversible chemical bridging between viral proteins and impurities, which are detrimental to the efficacy of the purification operations and product quality. For this reason, live infectious viruses are first at least partially purified in the prior art, e.g. by zonal ultracentrifugation, and then inactivated (U.S. Pat. No. 6,048, 537). The formalin inactivation step has been validated with established analytical procedures.

Complementing formalin treatment, UV inactivation has been considered for integration into the manufacturing process. The use of ultraviolet irradiation-inactivation for human vaccines has been demonstrated before for unenveloped and enveloped virus (US 2006/0270017). As the viral genome is more susceptible to UV-damage than viral surface antigens, UV-inactivation was shown to have little negative effect on the biochemical characteristics or immunogenicity of the product. The targets for UV inactivation are primarily nucleic acids in contrast to proteins which are targeted by formalin.

By combining formalin and UV-inactivation, scientists tried to overcome the limitations of isolated UV-inactivation or formalin-inactivation, respectively, when inactivating particularly resilient virus families.

Alternatively, many manufacturers use a detergent-based process step to both inactivate the live virus and to modify the virus. These detergent-based processes disrupt the lipid envelope of influenza viruses to yield either split (partially disrupted) or sub-unit (fully disrupted) vaccine antigen. Detergent treatment often reduces the reactivity of the virus antigen, and thus reduces unwanted side effects during vaccination. The detergent treated virus may be further inactivated by, e.g., formalin treatment. Examples of these methods may be found in U.S. Pat. No. 6,048,573, U.S. Pat. No. 4,522,809, and WO 02/09702. A disadvantage in this approach is that the virus undergoes various purification steps prior to the disruption step, and thus live infectious virus is handled by manufacturing personnel at several stages. This is of especial concern when vaccine against especially virulent forms of influenza, such as H5N1 strains, is being produced.

SUMMARY OF THE INVENTION

It is an object of the present invention to provide a method of producing viral vaccines with a reduced number of steps requiring the handling of infectious material, while producing viral antigens of decreased reactivity.

Therefore the present invention provides a method for the manufacture of a preparation comprising virus antigens comprising a) inoculation of cells with infectious virus in a fluid, b) propagation of said virus in said cells, c) collecting said propagated virus in the cell culture supernatant, d) inactivating said collected virus, and e) treating said inactivated virus with a detergent, resulting in a preparation comprising viral antigens.

In a second aspect a method for the manufacture of a preparation is provided comprising viral antigens comprising a) obtaining a fluid comprising infectious virus, b) completely inactivating said collected virus, c) treating said inactivated virus with a detergent, and d) purifying said inactivated virus resulting in a preparation comprising viral antigens.

Other aspects of the invention provide vaccine preparations prepared from the viral antigens produced according to the methods of the invention.

In another aspect the present invention provides the method of increasing the resistance to a viral infection in a subject comprising manufacturing a preparation comprising viral antigens and administering said preparation to a subject.

DETAILED DESCRIPTION OF THE INVENTION

Figure 1A:
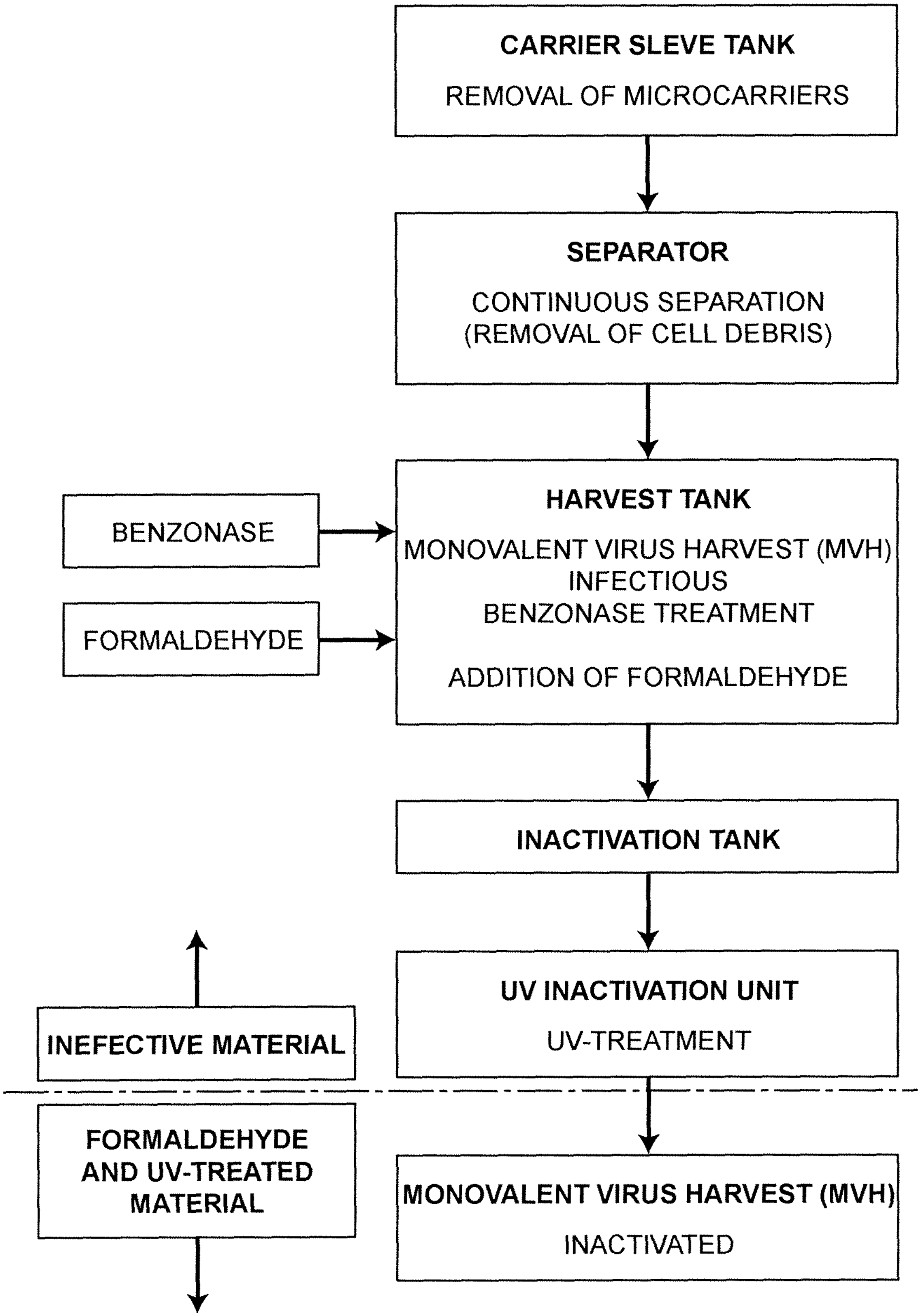
FIG. 1*a* shows a flow chart of the inventive procedure from virus collection after propagation to the inactivated harvest.
Figure 1B:
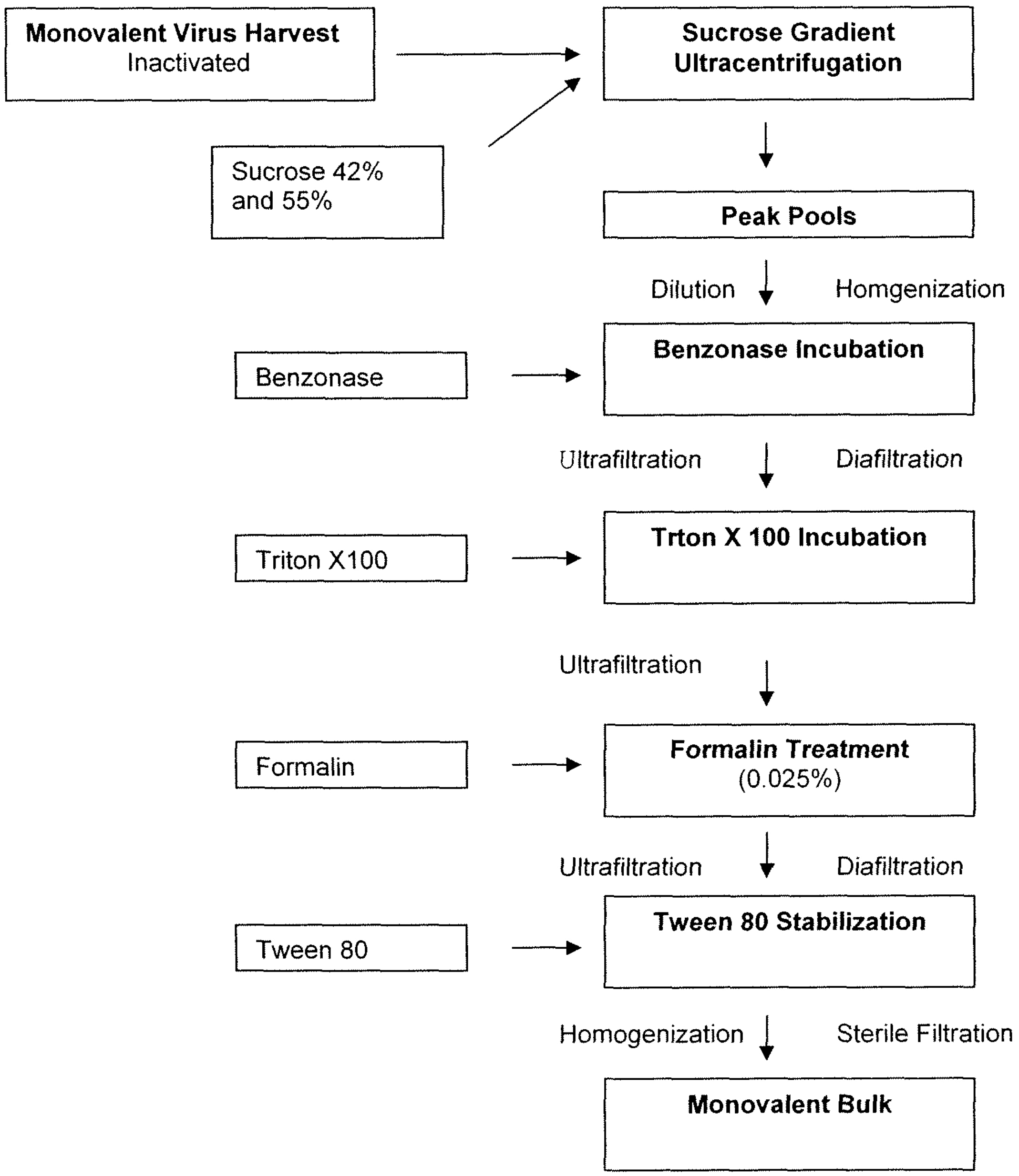
FIG. 1*b* shows a continuation of the flow chard of the inventive procedure from inactivated harvest to a monovalent bulk preparation.

Provided is a method for the manufacture of a preparation comprising virus antigens comprising a) inoculation of cells with infectious virus in a fluid, b) propagation of said virus in said cells, c) collecting said propagated virus in the cell culture supernatant, d) completely inactivating said collected virus, and e) treating said inactivated virus with a detergent, resulting in a preparation comprising viral antigens. Central to this procedure is that it is possible to reduce the number of steps performed on an active virus and thus the virus is inactivated after collection of the primary harvest prior to the detergent treatment and/or optional purification steps.

The “virus antigen” according to the present invention is a virus or portion of the virus which can induce an immune response in a subject against said antigen. Absolute success in the sense of completely immunising the subject is not required but this is to be understood in the sense of increasing the immune defence or immune response against said virus which reduces the chance of developing a disease associated with said virus after further exposure. Such a virus antigen can, e.g., be a whole inactivated virus, a split virus, a modified virus, viral proteins, in particular surface proteins, like haemagglutinin or neuraminidase. A “vaccine” is a preparation of said virus antigen in a form for administration, such as for injection, nasal, or transdermal administration. “Purification” according to the present invention relates to steps of removing non-viral constituents of the harvest fluid. The harvest fluid obtainable after the collection step is preferably a clarified supernatant, wherein solid or large impurities, e.g. remaining intact cells or cell debris of infected cells which break up during virus propagation, are removed by precipitation, e.g. via centrifugation. Therefore “collecting” refers to any steps that yield whole infectious viruses in a fluid, in particular clear fluid. Apart from removing cell debris the collection step can also include steps to remove other solid constituents of the cell growth medium or substrate e.g. any kind of substrate on which the cells are cultured. Propagated whole virus is released into said cell culture supernatant from which it can be collected. Therefore in a particular embodiment of the invention the step of collecting the propagated virus comprises separating the virus from the cells and/or cell debris of said cells after infection. This separation can, e.g., be facilitated by a low speed centrifugation of about 2000 g to 3000 g, up to 5000 g, 10000 g, 15000 g or 20000 g, which separates visible particles from the fluid. Alternately, the separation may be carried out by filtration. In particular preferred embodiments said fluid is substantially free of allantoin, collagen and/or albumin, such as ovalbumin, e.g. by choice of the cells used for virus propagation, e.g. mammalian, avian or insect cell cultures instead of embryonal eggs. In particular embodiments of the invention, African green monkey kidney (VERO) cells are used for viral propagation.

After the collecting step the virus is inactivated by any known means for virus inactivation, e.g. as disclosed in the US publication number 2006/0270017 A1, which is incorporated herein by reference. In particular, inactivation can be performed by formaldehyde treatment and/or UV irradiation, alone or in combination. As used in this application, “complete inactivation” or “completely inactivated,” as they refer to a viral preparation, means that the viral preparation does not contain plaque forming units (pfu,) as determined by culture of the viral preparation on chicken embryonic fibroblasts (CEF) or VERO cells.

One of the beneficial effects of the inventive methods is the reduction of steps which are performed on infectious viral media for which specific safety precautions are required. In the state of the art it was considered to be necessary to perform a purification step on the primary harvest to remove or substantially reduce non-viral proteins or nucleic acids which could cross-link with the virus during formalin treatment. This prejudice was overcome with the present invention which showed that it is indeed possible or even advantageous to inactivate directly after collection of the virus prior to the purification. To avoid such adverse reaction during inactivation the virus containing fluid, or its non-viral constituents, is (are) preferably not further concentrated or concentrated by a factor of below 10, 9, 8, 7, 6, 5, 4, 3 or 2 during or after the collection step. Preferably the concentration of non-viral protein and/or DNA of the native supernatant from the cell culture is maintained prior to the inactivation step. In particular embodiments the whole protein or non-viral protein concentration is in the range of μg/ml, such as below 950 μg/ml, 900 μg/ml, 850 μg/ml, 800 μg/ml, 700 μg/ml, 650 μg/ml, 600 μg/ml, 550 μg/ml, 500 μg/ml, 450 μg/ml, 400 μg/ml, 350 μg/ml, 300 μg/ml, 250 μg/ml, 200 μg/ml, 150 μg/ml, 100 μg/ml, 80 μg/ml, 60 μg/ml, 40 μg/ml, 30 μg/ml, 20 μg/ml, 10 μg/ml, 8 μg/ml, 6 μg/ml, 4 μg/ml, 3 μg/ml, 2 μg/ml or below 1 μg/ml, in the fluid during inactivation or after collecting the virus.

For the inactivation any amount of formaldehyde or UV irradiation dosage can be selected which are effective to inactivate the virus, alone or in combination. In a preferred embodiment of the present application the virus titer reduction due to the inactivation of the virus in the sample is at least about $1\times10^5$, in a more preferred embodiment, at least about $1\times10^7$ in a more preferred embodiment at least about $1\times10^{10}$, and in a most preferred embodiment at least about $1\times10^{14}$.

In a preferred embodiment of the present invention, the sample is treated with an effective concentration of formalin for about 12 to about 96 hours. In more preferred embodiments, the sample is treated with an effective concentration of formalin for about 24 to about 48 hours, and more preferably for about 24 to about 30 hours. In an especially preferred embodiment of the present invention, the sample is treated with an effective concentration of formalin for about 24 to about 24.5 hours. Those of skill in the vaccine arts will recognize that formalin concentration and treatment times may need to be optimised for the particular strain of virus treated in order to effect complete inactivation, wither alone or in combination with UV light. In a further embodiment the step of treating the sample with an effective concentration of formalin is carried out at about 10 to about 40° C. In an especially preferred embodiment of the pre-sent application the step of treating the sample with an effective concentration of formalin is carried out at about 32° C.

A preferred embodiment of the present invention includes the treatment of the sample with an effective concentration of formalin, wherein the effective concentration of formalin ranges preferably from about 0.01% to about 1% (w/w), preferably from about 0.01% to about 0.1% more preferably between about 0.025% and about 0.1% which corresponds to about 92 mg/l and about 368 mg/l formalin respectively when using a 37% formalin solution for adjusting the effective concentration.

In the present application the term “UV light” means ultraviolet radiation having a wavelength of 100 to 400 nm. The UV light may be selected from the group consisting of UV C (100 to 280 nm), UV B (280 to 320 nm), and UV A (320 to 400 nm). Photosensitizing agents like those which intercalate into the DNA and are activated by UV light, e.g. psoralens, may be used to enhance the inactivating effect of the UV radiation. In a preferred embodiment of the present invention the UV light is UV C having a wavelength of about 100 to about 280 nm. In a more preferred embodiment of the present invention the UV light has a wavelength from about 240 to about 290 nm. In an especially preferred embodiment of the present invention about 85% or more of the UV light have a wavelength of about 254 nm.

The UV light emission may be a continuous form of UV light emission, e.g. mercury lamp technology, or pulsed UV light, e.g. monochromatic laser technology. The desired UV intensity may be generated by combining two or more lamps. The subject matter of the invention encompasses any effective dose of UV light, i.e. any dose of UV light which safely inactivates a given virus preferably when combined with a formalin treatment. Those of skill in the vaccine arts will recognize that UV light wavelength and exposure may need to be optimised for the particular strain of virus treated in order to effect complete inactivation, either alone or in combination with formalin treatment. The effective dose may depend on a variety of factors which are generally known in the field, e.g. the physical parameters of the UV inactivation chambers such as size and diameter of the lamp and the chamber, distance between the virus containing medium and the UV light source, light absorption and reflection properties of the material of the chamber. By the same token, the wavelength and intensity of the UV C light as well as the contact time the virus is exposed to the UV light is also critical for the effective dose. Furthermore, the effective dose is also influenced by the virus itself, the medium containing the virus and their light absorption properties. Preferably, the effective dose is sufficient for inactivating at least 99.99% of virus contained in the sample, more preferably inactivating the virus to a level where no active virus is detected in a mammalian or avian cell culture test, or completely inactivated. In a preferred embodiment using UV C light a sample containing the virus is exposed to an effective dose ranging from about 5 to about 200 $mJ/cm^2$. In a preferred embodiment the effective dose is in the range of about 20 to about 100 $mJ/cm^2$, and in other preferred embodiments the effective dose in the range of about 40 to about 90 $mJ/cm^2$. In a preferred embodiment, the effective dose reduces an initial virus titer by $1\times10^5$. In bulk vaccine inactivation, the effective dose should be sufficient to eliminate any residual live virus which may be present after the chemical (formalin) inactivation step. As illustrated in the examples, this may be determined by very sensitive mammalian cell culture infection tests, such as the Vero cell culture test described in Example 1.3.

After inactivation the virus antigens are purified. The purification is preferably performed by ultracentrifugation at e.g. in the range of about 100000 g such at least 50000 g, 60000 g, 70000 g, 80000 g, or 90000 g, or up to 200000 g, 180000 g, 160000 g, 140000, g 120000 g or 110000 g. The ultracentrifugation method is commonly known in the art and is used in the routine manufacture of viral vaccines as e.g. described in the U.S. Pat. No. 6,048,537, which is thus incorporated by reference. Preferably the ultracentrifugation is performed in a sucrose density gradient which establishes itself during the centrifugation. In particular preferred embodiments the sucrose gradient is formed by using a solution of about 42% to 55% (w/w-%) sucrose (or any other adequate carbohydrate or sugar known in the art). For ultracentrifugation a continuous flow centrifuge may be used. The parameters for fractionating after ultracentrifugation are dependent on the characteristics of the virus strains used. The parameters for collection of the peak pool fractions are evaluated and determined individually for each virus strain and are in the range of about 46-50% to 34-38% sucrose. Preferably non-viral material (e.g. at this stage whole inactivated virus) are removed by density separation. Cell membrane fragments, including liposomes and proteins each have a characteristic specific density. Viruses as being a characteristic composition of proteins, nucleic acids and in the case of enveloped viruses also membrane can be purified by their specific density from non-viral material. In particular the whole viral antigens may be purified from incomplete virus portions, or vice versa.

This step of purifying the inactivated virus comprises at least partially removing soluble non-viral material from the virus. In particular the soluble non-viral material comprises cell proteins or cell nucleic acids from the cell of the original cell medium or culture. Non-viral material, including incomplete virus portions, is preferably reduced by an amount of at least 20%, preferably at least 25%, 30%, 35%, 40%, 45%, 50%, 55%, 60%, 65%, 70%, 75%, 80%, 85% or at least 90% during purification.

In particular preferred embodiments the collected fluid is treated with a nuclease to degrade nucleic acids of the host cells. Such a nuclease can be e.g. BENZONASE®.

In a further embodiment of the present invention, the cells use for cell culture and viral propagation may be primary cells or any cultured cell line suitable for producing the virus. Examples of cells which may be used include mammalian cells (e.g., CHO, BHK, VERO, HELA, or perC6 cells), avian cells (e.g, chicken embryo fibroblasts, or continuous cell lines from an avian) and insect cells (e.g, Sf9 cells). In particular preferred embodiments the cells are in form of a cell culture. The inventive method allows effective purification, including splitting of the material despite of the potential cross linking properties of the previous inactivation reagents. In contrast to egg grown virus, cell culture derived virus is of higher initial purity and is free of albumin and collagens, which represents an important advantage for the purification of the formalin treated harvest. The innovative formulation of the resulting product is free of flocculation without any need for stabilizers such as tocopherol or laureth-9.

In the present invention, the viruses to be inactivated are selected from enveloped DNA or RNA viruses, with single or double (DNA) stranded genomes, sense or antisense, continuous or segmented. In preferred embodiments of the invention, the viruses are selected from the group of enveloped viruses, including, flaviviruses, togaviruses, retroviruses, coronaviruses, filoviruses, rhabdoviruses, bunyaviruses, orthomyxoviruses, paramyxoviruses, arenaviruses, hepadnaviruses, herpesviruses, and poxviruses. In other preferred embodiments, the viruses are flaviruses, coronaviruses, orthomyxoviruses, or togaviruses. Particularly preferred are enveloped viruses such as influenza, including strains of influenza A, B or C, West Nile, and Ross River viruses (RRV.) In other preferred embodiments of the invention, the viruses are selected from the group of enveloped RNA viruses, including, flaviviruses, togaviruses, retroviruses, coronaviruses, filoviruses, rhabdoviruses, bunyaviruses, orthomyxoviruses, paramyxoviruses, and arenaviruses. In one particularly preferred embodiment, the virus is selected from the orthomyxoviruses, for example, an influenza virus strain: influenza virus strains may have varying combinations of hemaglutianin and neuraminidase surface proteins. In another particularly preferred example, the virus is selected from the togaviruses, for example an alphavirus such as the RRV) Another preferred group of viruses for use as the bulk viral solution are the coronaviruses, including the virus associated with Severe Acute Respiratory Syndrome (SARS). Another group of preferred viruses are the flaviviruses, including Japanese Encephalitis, tick borne encephalitis (TBE), Dengue fever virus, yellow fevers virus, West Nile Virus and hemorrhagic fever virus. Another preferred group of viruses are the poxviruses, including orthopox-viruses (such as vaccinia or modified vaccinia Ankara viruses), and avipoxviruses.

In further embodiments the purified virus is further processed. After purification further steps can comprise dilution of the purified virus, in particular after sucrose ultracentrifugation in order to dilute the viscous peak pool fraction which is expected to contain about 40% sucrose. The purified virus can be homogenized, additionally nuclease treated, pressure and/or ultra/diafiltrated.

In embodiments of the invention, the virus is modified by detergent treatment to produce a modified whole virus or split virus vaccine. The modification of the lipid envelope of the virus is carried out by solubilisation with a detergent such as TRITON X100® (in a concentration suitable to destabilize or disintegrate the virus, in particular the viral lipid envelope membrane. The detergent treatment will at least in part remove the membrane of said virus. Preferably the detergent con-centration is removed, e.g. by diafiltration or chromatographic processes. Detergents for use in the detergent treatment step include ionic (cationic, anionic, zwitterionic) detergents or non-ionic detergents. Suitable detergents include the TWEEN® (polysorbate) group of detergents (e.g., TWEEN 80®), and the TRITON® group of detergents (e.g., TRITON 100®.)

Optionally, the viral antigen preparation is further stabilized by an additional formaldehyde treatment or stabilizer addition such as by usage of detergents as disclosed in the WO 02/097072 A2 which is incorporated herein by reference. Such detergents are for example detergents suitable to stabilize the HA protein, such as polysorbate 80 (TWEEN 80®), Octylphenolpoly(ethyleneglycolether) (TRITON X100®), deoxycholate, laureth-9 and tocopherol. It is thought that surface proteins are kept solubilized by complex micelles of membrane constitu-ents and the detergents.

In particular preferred embodiments the virus is further processed to a split virus comprising any one of the following steps of dilution, homogenisation, nuclease treatment, pressure filtration, ultra/diafiltration, solubilisation, diafiltration, stabilization by formaldehyde treatment, dilution, ultra/diafiltration, (detergent) stabilizer addition, a second homogenisation and sterile filtration.

In other particular preferred embodiments the virus is further processed to a modified virus preparation comprising any one of the following steps of dilution, homogenisation, nuclease treatment, pressure filtration, detergent treatment, ultra/diafiltration, stabilizer addition, a second homogenisation and sterile filtration. In particular the detergent stabilization is performed to introduce a detergent into the viral membrane in the case of enveloped virus to increase the stability of the complete virus, which is thus modified.

In additional embodiments the virus is processed to a subunit vaccine comprising the isolation of single viral subunits or viral proteins, in particular surface proteins like haemagglutinin or neuraminidase. The isolation can e.g. be performed by affinity purification and/or chromatographic methods such as ion exchange chromatography.

Surprisingly the method of the present invention is suitable for industrial scale production of virus antigen vaccines. Therefore preferably the inactivation or any other step such as the inoculation, the propagation the collection or the purification is performed on amounts or yields amounts of at least 0.5 l, 1 l, 2 l, 3 l, 4 l, 5 l 6 l, 7 l, 8 l, 9 l, 10 l, 12 l, 14 l, 16 l, 18 l, 20 l, 25 l, 30 l, 35 l, 40 l, 60 l, 80 l, 100 l, 120 l, 140 l, 160 l, 180 l, 200 l of a fluid comprising a virus or viral antigen.

In a further aspect the present invention also provides a method for the manufacture of a preparation comprising viral antigens comprising a) obtaining a fluid comprising infectious virus, b) completely inactivating said collected virus, c) treating said inactivated virus with a detergent, d) purifying said inactivated virus resulting in a preparation comprising viral antigens. Of course it is also possible to use infectious virus containing fluids per se, which can be from any cell supernatant as described above, for inactivation, detergent treatment, and purification. Preferably said fluid comprising infectious virus is obtained from a cell culture.

In particular preferred embodiments the virus antigens, in particular split virus or modified virus antigens, are stabilized by addition of an effective amount of TWEEN 80®, in par-ticular preferred at a concentration of about 0.125%, e.g. above 0.01%, 0.05% or 0.4%, and below 0.6%, 0.5%, 0.4%, 0.3%, or 0.2%. Therefore the present invention also provides in a further aspect the method of stabilizing viral antigens by addition of TWEEN 80®. According to the present invention it was found that as a detergent TWEEN 80® is less potent to solubilize viral membranes as TRITON X 100® but is by far more biocompatible and can be present in a vaccine preparation. The effective amount to stabilize viral antigens is preferably below the amount to solubilize viral membranes as in the split virus solubilization procedure using high concentrations of TRITON X100® of e.g. 0.5%. In other embodiments the viral antigens are free of stabilizers. In particular embodiments a production of a split vaccine is provided by a process where the virus harvest is fully inactivated prior to the splitting and purification process. Surprisingly, the inactivation process with formalin treatment and UV treatment does not interfere with the subsequent detergent treatment and purification processes.

In further embodiments a vaccine or pharmaceutical composition is provided which comprises one or more viral antigens. Such a pharmaceutical composition can further comprise a pharmaceutical carrier and/or an adjuvant. Such pharmaceutical carriers are for example stabilising salts, emulators, solubilisers or osmo-regulators, suspending agents, thickening agents, redox components maintaining a physiological redox potential. Preferred adjuvants include aluminium salts, microemulsions, lipid particles, and/or oligonucleotides used to increase the immune response. A further aspect of the present invention is a pharmaceutical composition or preparation as vaccine comprising an antigen. A vaccine can be used e.g. for an injection as a prophylactic means against a virus associated disease. In particular preferred embodiments the composition or vaccine comprises more than one antigen, e.g. 2, 3, 4, 5, 6, 7 or 8, in particular of different virus strains, subtypes or types such as influenza A and influenza B, in particular selected from of one or more of the human H1N1, H2N2, H3N2, H5N1, H7N7, H1N2, H9N2, H7N2, H7N3, H10N7 subtypes, of the pig flu H1N1, H1N2, H3N1 and H3N2 subtypes, of the dog or horse flu H7N7, H3N8 subtypes or of the avian H5N1, H7N2, H1N7, H7N3, H13N6, H5N9, H11N6, H3N8, H9N2, H5N2, H4N8, H10N7, H2N2, H8N4, H14N5, H6N5, H12N5 subtypes.

Suitable adjuvants can be selected from mineral gels, aluminium hydroxide, surface active substances, lysolecithin, pluronic polyols, polyanions or oil emulsions such as water in oil or oil in water, or a combination thereof. Of course the selection of the adjuvant depends on the intended use. E.g. toxicity may depend on the destined subject organism and can vary from no toxicity to high toxicity.

Another preferred embodiment of the composition or vaccine of the present invention further comprises buffer substances. Buffer substances can be selected by the skilled artisan to establish physiological condition in a solution of the composition according to the invention. Properties like pH and ionic strength as well as ion content can be selected as desired.

A further preferred composition or vaccine according to the invention, comprises a pharmaceutically acceptable carrier.

The term "carrier" refers to a diluent, e.g. water, saline, excipient, or vehicle with which the composition can be administered. For a solid composition the carriers in the pharmaceutical composition may comprise a binder, such as microcrystalline cellulose, polyvinylpyrrolidone (polyvidone or povidone), gum tragacanth, gelatine, starch, lactose or lactose monohydrate; a disintegrating agent, such as alginic acid, maize starch and the like; a lubricant or surfactant, such as magnesium stearate, or sodium lauryl sulphate; a glidant, such as colloidal silicon dioxide; a sweetening agent, such as sucrose or saccharin.

Also provided is the method of increasing the resistance to a viral infection in a subject comprising manufacturing a preparation comprising one or more different viral antigens and administering said a preparation comprising one or more viral antigens as described above to a subject. The preparation is preferably a vaccine. It is also contemplated to provide the virus antigens as prepared by the present invention as a vaccine or for increasing the resistance to a viral infection in a subject by administering said virus antigens.

EXAMPLES

Example 1

Inactivation of Infectious Virus

Three different influenza strains, two A-strains Hiroshima (HR, H3N2), a New Calcdonia (NC, H1N1) and a B-strain, Malaysia (MA), were produced in Vero cell cultures. After virus propagation the infectious virus harvest is inactivated prior to purification as given in the flow chart of FIG. 1*a*.

1.1. Formalin Inactivation

The first inactivation step with formalin is carried out on a cell-free, infectious monovalent virus harvest, i.e. a bioreactor harvest after clarification via centrifugation. After the collection at 30 to 34° C., the monovalent virus harvest is treated with about 0.9 to about 1.1 U/ml BENZONASE™ (Endonuclease from *Serratia marcescens*) at 30 to 34° C. for 4 to 8 hours. Then it is treated with <=92 mg/l formalin for 24 to 24.5 hours at 32+/−2° C.

1.2. UV Inactivation

A number of inactivation experiments with formalin-inactivated viruses are carried out using an inactivation chamber with a 65 W UV lamp and a thin layer chamber. Although full inactivation of monovalent virus harvest can be demonstrated when using flow rates of 100 liter per hour for three cycles, this setup did not allow the on-line measurement of the UV signal. The Vero cell culture medium used for Influenza production contains various organic compounds responsible for absorption of the UV signal. Therefore, the system, is equipped with a 110 W lamp allowing a continuous monitoring of the UV signal during monovalent virus harvest treatment.

Formalin treated monovalent Influenza Panama harvest is used as a model substrate for the inactivation. For continuous inactivation with thin layer UV technology a WEDECO VISA system (Germany) equipped with a VISA lamp (110 W) is used. The UV thin layer chamber is a stainless steel 1.4435 device with a 30 mm diameter quartz tube. A calibrated UV sensor allows on-line control of the UV signal. The UV thin layer chamber is operated at a flow rate of 240+/−10 liter per hour at ambient temperature. The flow rate conditions are controlled by a calibrated flow-meter. The monovalent harvest is exposed to 10 UV cycles. After each cycle 20 liter of the UV treated monovalent harvest is removed and further purified by sucrose gradient purification using continuous ultracentrifugation.

1.3. Safety Test

The standard Vero safety test is a highly stringent quality test for the residual infectivity of inactivated influenza strains. The test is also applicable to other viruses. A monovalent bulk product, i.e. purified virus antigen after sucrose gradient centrifugation and ultra-diafiltration, is added to 5 Roux flasks (4 ml/flask). After incubating for 7 days at 32° C. in Vero culture medium, the cell cultures are harvested, pooled and added to 5 Roux flasks (10 ml/flask). After another incubation step for 7 days at 32° C., the cell cultures are harvested, pooled, and tested for hemagglutinin (HA).

The HA-test is based on the fact that Influenza viruses can bind erythrocytes using their surface protein hemagglutinin. The test is carried out in a sterile environment. A suspension of Influenza viruses with a defined HA titer serves as a positive control and a 0.9% NaCl solution serves as a negative control. 50 µl of a 1:2 dilution in 0.9% NaCl of a sample to be tested are given into one well of a 96-well plate. To each well 50 µl of a solution containing chicken erythrocytes is added. Subsequently, the plates are incubated for 30 to 45 minutes at room temperature. Then the hemagglutination is visually determined, wherein, if five wells containing the same sample do not show any hemagglutination, the sample passed the HA test.

Example 2

Purification by Ultracentrifugation

During purification of influenza virus antigen, the monovalent harvest (MVH) is concentrated by centrifugation. A continuous flow centrifugation procedure can be applied for the manufacture of the Vero cell culture grown viral vaccine based on a sucrose gradient formed using an aqueous sucrose solution. The centrifuge model used was equipped with a preclarifier. Small scale experiments with a density gradient formed using approx. 42% and 55% (w/w) sucrose solution in 20 mM Tris-buffer were carried out under different centrifugation conditions. In addition, ultracentrifugation without preclarifier but with increased g-forces turned out to be a valuable tool for yield improvement.

Monovalent Influenza virus harvests (MVHs) were used for the comparative studies. The MVHs were purified with continuous ultracentrifugation with a laboratory centrifuge model RK-6 at 35.000 rpm.

Example 3

Purification/Processing

For an influenza candidate vaccine, three different strains of influenza were purified and collected from ultracentrifugation as described in example 2. Antigen yields were different in the Peak Pools. The influenza strain New Calcdonia had the lowest antigen yield followed by Hiroshima and finally Malaysia. Protein content was highest in the Malaysia and lowest in the Hiroshima. SRD (Single Radial Immunodiffusion Assay (HA-quantification)) to Total Protein ratios were comparable in Peak Pools from Malaysia and New Calcdonia, but higher in the Hiroshima (Table 1).

TABLE 1

Analytical results of peak pools

| Influenza strain | HR05/61 Hiroshima | MA04/61 Malaysia | NC99/51 New Caledonia |
|---|---|---|---|
| Amount (ml (g)) | 840.4 (1000) | 420.2 (500.1) | 420.2 (500) |
| SRD (µg/ml) | 246.2 | 426.6 | 194.9 |
| Protein conc. (µg/ml) by Bradford | 487 | 1495 | 764 |
| SRD/protein ratio | 0.51 | 0.28 | 0.26 |

TABLE 1-continued

Analytical results of peak pools

| Influenza strain | HR05/61 Hiroshima | MA04/61 Malaysia | NC99/51 New Caledonia |
|---|---|---|---|
| VERO Protein conc. (µg/ml) by ELISA | 6.2 | 19.7 | 18.9 |

Further processing was according to the following overview:

3.1. Dilution of Peak Pools

The Peak Pools are diluted 3 fold with TBS buffer to reduce sucrose concentration for reduction of viscosity.

3.2. First Homogenization Peak Pool

The diluted Peak Pool is treated with a high pressure homogenizer "NS 1001L Panda" (Niro Soavi S.p.A.). The virus suspension is passed through the homogenizer 3 times with 800 bar. This pressure is sufficient to improve subsequent processing steps by disrupting virus aggregates.

3.3. BENZONASE® Addition

BENZONASE®, a recombinant nuclease produced in *E. coli*, is added to the virus suspension at a final concentration of 3 U/ml to degrade cell derived DNA.

3.4. Pressure Filtration

After BENZONASE® addition, a 0.22 µm pressure filtration is performed to keep the virus suspension free of advantitious organisms such as bacteria during the subsequent incubation period. Incubation is performed at 32° C. over night.

3.5. Ultra/Diafiltration

After BENZONASE® incubation is finished, Ultra/Diafiltration is performed with a 30 kD suspended channel ultrafiltration mem-brane (Pall) with a filtration area of 0.1 m2 at small scale and 0.5 m2 at pilot scale, The Ultraretentate is diafiltrated with 10 Retentate volumes of TBS (Tris buffered saline)+0.008% TRITON X100® (w/w).

3.6 TRITON X100® Addition for Solubilization and Incubation

For Virus splitting, TRITON X100® is added to a final concentra-tion of 0.5% and incubated over night at room temperature.

3.7. Diafiltration II

For removal of the high TRITON X100® concentration, Diafiltration is performed with a 30 kD suspended channel ultrafiltration membrane (Pall). The Ultraretentate is diafiltrated with 15 retentate volumes of TBS (Tris buffered saline).

3.8. Formaldehyde Addition and Incubation

Formalin is added into the Ultra/Diaretentate to a final concentration of 0.025% for antigen stabilization. The incubation is performed for 18-24 hours at room temperature. Formalin is a saturated aqueous solution of ~36-37% formaldehyde gas.

3.9. TRITON X100® Concentration Determination by HPLC

Subsequent processing steps consist of a dilution step and a further Ultra/Diafiltration. In order to be able to dilute the UDR below the CMC for TRITON X 100 (TX 100®, ~0.015%, 250 µM, in aqueous solution), an analytic TX 100® determination step was introduced to define the concentration of TX 100®. The dilution factor is dependent on this TX 100® concentration.

3.10. Dilution of the UDR Below the Critical Micellar Con-centration for TX 100®

The Ultra/Diaretentate containing residual TX 100 of about 0.1-0.2% (determined by HPLC) is diluted with TBS to a final TX 100® concentration of 0.008%, a concentration clearly below the CMC (Critical Micellar Concentration).

3.11. Ultra/Diafiltration III

Ultra/Diafiltration is performed with the identical 30 kD sus-pended channel ultrafiltration membrane. The Ultraretentate is diafiltrated with 5 Retentate volumes of TBS (Tris buffered saline)+5 VC TBS+0.008% TRITON X100® (w/w).

3.12. Detergent Stabilisation

Alter reduction of the TX 100® concentration to the target level, TWEEN80® is added into the suspension to a final concentration of 0.125%±0.025% for further virus antigen stabilization. This avoids antigen re-aggregation due to too low TX 100® concentrations.

3.13. Second Homogenization

A second high pressure homogenization step is carried out to keep antigen loss low at the 0.22 µm filtration step. The same homogenizer as described in section 3.2 with identical settings is used.

3.14. Sterile Filtration

Following the 2nd homogenization step a sterile filtration is carried out using 0.22 µm filters (Millipore). The sterile filtered Bulk material is termed Monovalent Bulk (MVB).

Example 4

Results

TABLE 2

Results from purification after ultracentrifugation as exemplified for a split virus (Hiroshima):

| | | Peak pool | DIL (1:3) | HOM1 | PFIL | UDR1 30K | UDR2 30K | UDR | HOM2 | MVB |
|---|---|---|---|---|---|---|---|---|---|---|
| Amount | g | 500 | 1501.6 | 1479.8 | 1537.5 | 410.4 | 411.7 | 421.8 | 414.9 | 421.5 |
| Optical density | OD, 405 nm | / | 0.82 | 0.24 | 0.20 | 0.86 | 0.72 | 0.88 | 0.18 | 0.15 |
| SRD (NIBSC) | µg/ml | 194.9 | 58.7 | 56.1 | 52.9 | 130.9 | 110.3 | 84 | 86.5 | 74.6 |
| SRD total | mg | 81.9 | 77.4 | 78.2 | 73.9 | 53.7 | 45.4 | 35.4 | 35.9 | 31.5 |
| Protein | µg/ml | 764 | / | / | / | / | / | / | / | 385 |
| Protein total | mg | 382 | / | / | / | / | / | / | / | 162.3 |
| VERO Protein conc. | µg/ml by ELISA | 18.9 | 4.5 | 4.4 | 3.8 | 10.8 | 6.3 | 4 | 5 | 4.7 |
| Total VERO Protein | mg by ELISA | 8 | 6.1 | 5.9 | 5.2 | 4.4 | 2.6 | 1.7 | 2.1 | 2 |
| Vero DNA | ng/ml | / | / | / | / | / | / | / | / | 0.64 |
| Vero DNA total | µg | / | / | / | / | / | / | / | / | 0.27 |
| TX100 | (%) | / | / | / | / | 0.482 | 0.101 | 0.018 | 0.017 | 0.017 |
| Tween80 | (%) | / | / | / | / | / | / | / | / | 0.115 |

DIL (1:3) . . . dilution of peakpool; UDR . . . Ultradiaretentate after ultradiafiltration; HOM-1, HOM-2 . . . homogenization 1 and 2; PFIL . . . 0.22 µm pressure-filtration; MVB . . . monovalent bulk The total SRD in the MVB was 73 mg. Total Vero protein levels were reduced from 5.2 mg to 1 mg, a reduction of 80.8%. Total Vero DNA was reduced to 0.28 μg in the MVB. Total protein was reduced from 487 mg to 212 mg constituting a reduction of 56.5%.

Similar results were obtained for the Malaysia strain: Total Vero protein could be reduced from 8.3 mg to 2.4 mg, which is a reduction of approximately 67.5% from the Peak Pool to the MVB. Vero DNA content in the MVB was 1.8 μg. Reduction of Total Protein during purification was 58.6% from 748 mg to 310 mg.

For the New Calcdonia strain at the end of purification, total Vero protein could be reduced from 8 mg in the Peak Pool to 2 mg in the MVB, which is a reduction of 75%. Total Vero DNA content in the MVB was 0.27 μg. Total protein was reduced from 382 mg in the Peak Pool to 162 mg in the MVB, which constitutes a reduction of 57.6%.

The purification process is very consistent and robust. A highly purified virus preparation resulted from the successful reduction of host cell protein and DNA as well as process chemicals like BENZONASE®, Sucrose, Formaldehyde and TRITON X100® as well as the lack of Endotoxins. All preparations were sterile after production. SRD to protein ratios complied with specifications in all three MVBs.

The invention claimed is:

1. A method for the manufacture of a preparation comprising virus antigens comprising a) inoculating cells with infectious virus in a fluid, b) propagating said virus in said cells, c) collecting said virus propagated in said cells, d) completely inactivating said virus collected from said cells, e) purifying the inactivated virus, wherein the purification comprises ultracentrifugation or use of a sucrose gradient, f) contacting the purified virus with a nuclease, and g) treating said virus with detergent under conditions effective to yield a split virus, resulting in a preparation comprising viral antigens, wherein the collected virus of step (c) is not purified prior to the inactivating step.

2. The method of claim 1, wherein the step of collecting said propagated virus comprises separating the virus from said cells and/or cell debris of said cells after infection.

3. The method of claim 1, wherein said inactivating is performed by addition of formaldehyde.

4. The method of claim 1, wherein said inactivating is performed by UV irradiation.

5. The method of claim 1, wherein said virus propagated in said cells is released into said fluid.

6. The method of claim 1, wherein step (c) or (d) further comprises treating the virus with a nuclease.

7. The method of claim 6, wherein said nuclease is Benzonase®.

8. The method of claim 1, wherein said cells are in form of a cell culture during said virus propagation.

9. The method of claim 1, wherein said cells are mammalian or avian cells.

10. The method of claim 1, wherein said cells are epithelial cells.

11. The method of claim 8, wherein said cells are Vero cells.

12. The method of claim 1, wherein said virus is an enveloped virus.

13. The method of claim 12, wherein said virus is an orthomyxo virus.

14. The method of claim 13, wherein said virus is an influenza virus.

15. The method of claim 1, wherein the concentration of non-viral protein during said inactivation is below 350 μg/ml.

16. The method of claim 1, wherein said manufacture is on industrial scale amounts.

17. The method of claim 16, wherein said inactivation is performed on at least 1 L virus containing fluid.

18. A method for the manufacture of a preparation comprising viral antigens comprising a) obtaining a clarified supernatant comprising infectious virus, b) inactivating said virus from step (a), c) purifying the virus, wherein the purification comprises ultracentrifugation or use of a sucrose gradient, d) contacting the inactivated, purified virus with a nuclease, e) treating said virus with detergent under conditions effective to yield a split virus, and f) further purifying said virus resulting in a preparation comprising viral antigens, wherein the clarified supernatant comprising the infectious virus is not purified prior to the inactivating step.

19. The method of claim 18, wherein said clarified supernatant is obtained from a cell culture.

20. The method of claim 19 further comprising the step of stabilizing said viral antigens.

21. The method of claim 20, wherein said viral antigens are stabilized by addition of an effective amount of Tween 80® (polysorbate 80).

22. The method of claim 21, wherein Tween 80® is in an amount of about 0.125%.

* * * * *